（12） United States Patent
Su (10) Patent No.: US 9,926,028 B2
(45) Date of Patent: Mar. 27, 2018

(54) ASSEMBLY OF A LIGHT AND A WATCH OF A BICYCLE CAPABLE FOR ADJUSTING ANGLE

(71) Applicant: Tina Su, Taichung (TW)

(72) Inventor: Tina Su, Taichung (TW)

( * ) Notice: Subject to any disclaimer, the term of this patent is extended or adjusted under 35 U.S.C. 154(b) by 174 days.

(21) Appl. No.: 14/985,314

(22) Filed: Dec. 30, 2015

(65) Prior Publication Data
US 2017/0190371 A1    Jul. 6, 2017

(51) Int. Cl.
| B62J 6/00 | (2006.01) |
| B62J 6/02 | (2006.01) |
| F21V 33/00 | (2006.01) |
| F21V 23/04 | (2006.01) |
| A61B 5/00 | (2006.01) |
| A61B 5/0205 | (2006.01) |

(52) U.S. Cl.
CPC .............. *B62J 6/02* (2013.01); *A61B 5/0205* (2013.01); *A61B 5/681* (2013.01); *B62J 6/001* (2013.01); *F21V 23/0464* (2013.01); *F21V 33/0052* (2013.01)

(58) Field of Classification Search
CPC ........................................................ B62J 6/02
See application file for complete search history.

(56) References Cited

U.S. PATENT DOCUMENTS

| 3,225,982 | A * | 12/1965 | Melton | ........... | F21L 4/00 |
| | | | | | 224/183 |
| 6,428,192 | B1 * | 8/2002 | Chen | ........... | B62J 6/02 |
| | | | | | 362/191 |
| 7,192,169 | B2 * | 3/2007 | Takeda | ........... | B62J 6/003 |
| | | | | | 362/194 |
| 8,607,647 | B1 * | 12/2013 | Wilson | ........... | G01L 3/104 |
| | | | | | 73/862.08 |
| 9,290,223 | B2 * | 3/2016 | Lee | ........... | B62J 6/02 |
| 2005/0180150 | A1 * | 8/2005 | Okada | ........... | B62J 6/02 |
| | | | | | 362/473 |
| 2008/0285259 | A1 * | 11/2008 | Uke | ........... | F21L 4/00 |
| | | | | | 362/103 |
| 2010/0246199 | A1 * | 9/2010 | Ma | ........... | B62J 6/02 |
| | | | | | 362/474 |

* cited by examiner

*Primary Examiner* — Charlie Y Peng
(74) *Attorney, Agent, or Firm* — Rosenberg, Klein & Lee (57) ABSTRACT

An assembly of a light and a watch of a bicycle capable for adjusting angle comprises a mount and a light base. One side of the mount is mounted on the bicycle. A display screen is arranged at a top surface of the mount. A control member and a sensing member are arranged in the mount and electrically connected with the display screen. The sensing member is detected a variation of a rider and the bicycle to display on the display screen. One side of the light base is pivoted to a front end of the mount and the other end thereof has a light transparent portion. The light base is pivoted, rotated, and slid relative to the mount. The light base is electrically connected with the control member. The control member is for controlling a variation of a light beam of the light base. The mount is mounted on the bicycle so that the rider may see a display on the display screen and it is convenient to provide for lighting.

3 Claims, 10 Drawing Sheets

FIG.10

ASSEMBLY OF A LIGHT AND A WATCH OF A BICYCLE CAPABLE FOR ADJUSTING ANGLE

BACKGROUND OF THE INVENTION

1. Field of the Invention

The present invention relates to an equipment of a bicycle, and especially relates to an assembly of a light and a watch of a bicycle capable for adjusting angle. The rider is capable for recognizing the road condition in front of himself with light beam and further the relative information may be shown or displayed to make the rider know at any time. Besides it may save the space of the stein of the bicycle, the rider may keep safe.

2. Description of Related Art

The bicycle is important to a certain extent in recent society. Besides the rider may take exercise to strengthen, the emotions between people may be also improved. There are more and more people riding while they are free or in weekend. With the popularity of the bicycle, the peripheral products are risen gradually, such as fixing tools, replacing elements, electronic recorders, lights, and so on. The functions of many products are based on the use of the rider. The lights and the electronic recorders are uses mostly. The light may provide the rider to clearly see the road condition and environment to keep safe while riding in dark or poor visible place. The electronic recorder is mainly recorded the relative information of the rider or the bicycle, such as calorie, heartbeat, pulse of the rider or revolution per minute, riding distance, speed of the bicycle and further shown or displayed riding path or place. It is convenient for the rider while riding.

Please reference to Taiwanese patent no. M340798, it disclosed an exercise status detector. The detector comprises a shell base mounted on a bicycle or worn on a human body and having a display screen, a heartbeat detecting unit arranged on the shell base and detected a physical variation of the human body to output a heartbeat signal, a step counting unit arranged in the shell base and detected a walking status of the human body to output a step counting signal, and a micro processing unit arranged in the shell base. The micro processing unit may receive and process the heartbeat signal, the step counting signal, and a travel signal of a moving status of the bicycle to a travel data, a heartbeat data, and a step counting data to output and display on the display screen. It may produce many functions and make more practical and convenient. Please also reference to Taiwanese patent no. M433360, it disclosed a fastening structure for a bicycle. The structure comprises a fastening base, a retaining strip, a press-fit assembly, a stand, and a connection base. The fastening base has a receiving groove and a locking portion is arranged at a bottom portion of the fastening base. The retaining strip is arranged at a top portion of the fastening base. A stop section is arranged at one side of the retaining strip. The press-fit assembly has a threaded rod and a push block. The push block is arranged in the receiving groove. The threaded rod is passing through the fastening base and pivoted to the push block. The stand is provided the retaining strip to pass through. The connection base is assembled to a top surface of the stand which is connected with a construction member. According to above mentioned structure, the retaining strip is passing through the stand, bound to a frame tube, locked to the fastening base, and pressed-fit with the press-fit assembly to achieve the effect of firmly fastening. The stand and the connection base are replaceable.

However, the lights and the electronic recorders are generally mounted at the stein of the bicycle. It is mainly convenient for the rider to pay attention to the relative information at any time and truly light the direction in front of the rider. But too many electronic recorders and lights mounted on the stein of the bicycle make the total weight of the bicycle too heavy and untidy. Furthermore, in order to detect various messages and information, too many electronic recorders and lights make the cost much higher and the space of the stein of the bicycle is occupied very much. It has run in opposite direction about the objects of light weight and simplification. Therefore, how to put the electronic recorders and lights in order simply and cleanly so as not to influence the operation of each element is one of the most important tasks.

In view of the foregoing circumstances, the inventor has invested a lot of time to study the relevant knowledge, compare the pros and cons, research and develop related products. After quite many experiments and tests, the "assembly of a light and a watch of a bicycle capable for adjusting angle" of this invention is eventually launched to improve the foregoing shortcomings, to meet the public use.

SUMMARY OF THE INVENTION

The main object of this invention is providing an assembly of a light and a watch of a bicycle capable for adjusting angle. It may provide smooth operation and further make the location of the stein of the bicycle clear, simple, and uniform and save the space of the location of the stein to light the weight of the bicycle. Therefore, the riding speed may be improved and the disadvantage of the prior art which are occupying the space of the stein due to mounting various electronic recorders (such as dashboard camera, and so on) and lights to result in heavy weight and slowing down the riding speed may be also improved.

In order to achieve above mentioned object, an assembly of a light and a watch of a bicycle capable for adjusting angle comprises a base, one side thereof is mounted on the bicycle, a display screen is arranged at a top surface of the mount, a control member and a sensing member are arranged in the mount and electrically connected with the display screen, the sensing member is detected a variation of a rider and the bicycle to display on the display screen; and a light base, one side thereof is pivoted to a front end of the mount and the other end thereof has a light transparent portion, the light base is pivoted, rotated, and slid relative to the mount, the light base is electrically connected with the control member, and the control member is for controlling a variation of a light beam of the light base; wherein the mount is mounted on the bicycle so that the rider may see a display on the display screen and it is convenient to provide for lighting.

In some embodiments, one end of the mount pivoted to the light base is formed a concave groove and two convex ears respectively arranged at two side of the concave groove, one end of the light base pivoted to the mount protruded a pivoting block inserted into the concave groove, a pin rod is passing through the two convex ears and the pivoting block, and the pivoting block of the light base is pivoted up and down relative to the concave groove with the pin rod passing therethrough.

In some embodiments, one end of the mount pivoted to the light base has a ball groove, one end of the light base corresponding to the ball groove has a ball embedded block, the ball embedded block of the light base is pivoted in the ball groove, and the light base is rotated to change direction relative to the mount.

In some embodiments, one end of the light base corresponding to the mount is protruded a sliding block, one end of the mount corresponding to the light base has a sliding track, any one side surface of the mount corresponding to the sliding track has an opening fluidly communicated with an inside of the sliding track, the sliding block of the light base is slid into the sliding track from the opening, and the light base is transversely slid in one end of the mount due to the arrangement of the sliding block and the sliding track.

In some embodiments, a receiving unit is built in the sensing member of the mount, a ring tape is worn on the rider, a transmission unit and a detecting unit are built in the ring tape, the detecting unit is detected a change of the rider's body and transmitted a signal to the receiving unit of the sensing member through the transmission unit, the transmission unit is wirelessly transmitted the signal to the receiving unit of the sensing member for receiving and further the received signal is displayed on the display screen.

In some embodiments, a photosensing member is further arranged in the mount and electrically connected to the control member, the photosensing member is detected an ambient luminosity and then activated the control member to control intensity, focusing, and scattering of a light beam transmitted through the light transparent portion.

In some embodiments, a plurality of control buttons is arranged below the display screen, the control buttons are electrically connected to the control member, and each of the control buttons may control, fine tune, and set a value displayed on the display screen.

In conclusion, the advantages of the present invention are that the rider may read or check the value or relative information shown or displayed on the display screen, the total weight of bicycle may be lighted due to not many electronic recorders (such as dashboard camera and so on) and lights, the lighting position may be adjusted by the rider himself or herself what the rider wants, and the lighting types may be changed based on the brightness of the ambient light source. Besides it may save power, the rider may keep safe. Compared to the conventional bicycle which is mounted too many electric devices and lights, the present invention has practicability.

The various objects and advantages of the present invention will be more readily understood from the following detailed description when read in conjunction with the appended drawing.

DETAILED DESCRIPTION OF THE INVENTION

To describe clearly that the present invention achieves the foregoing object and function, the technical features and desired function are described with reference to a preferred embodiment and accompanying drawings.

Please reference to FIGS. 1 to 4 (for first embodiment), an assembly of the light and the watch of the bicycle capable for adjusting angle of the present invention may comprise a mount 1 and a light base 2. One side of the mount 1 is mounted on the bicycle 10. A display screen 11 is arranged at a top surface of the mount 1 for being seen by a rider. A control member 12 and a sensing member 13 are arranged in the mount 1 and electrically connected with the display screen 11. The sensing member 13 is detected a variation of a rider and the bicycle 10 to display on the display screen 11. One side of the light base 2 is pivoted to a front end of the mount 1 and the other end thereof has a light transparent portion 21. The light base 2 is pivoted, rotated, and slid relative to the mount 1. The light base 2 is electrically connected with the control member 12. The control member 12 is for controlling a variation of a light beam of the light base 2. Therefore, the mount 1 is mounted on the bicycle 10 so that the rider may see a display on the display screen 11 and it is convenient to provide for lighting. (The above mentioned embodiment is the main skill feature of this invention and corresponds to the claim 1 of this invention to understand the object and embodiments of this invention in detail. And the skill features of the depending claims are for describing the claim 1 in detail or adding more skill features, but not limited thereto. It should be known that the claim 1 is not necessary to include the skill features of the depending claims.)

Figure 1:
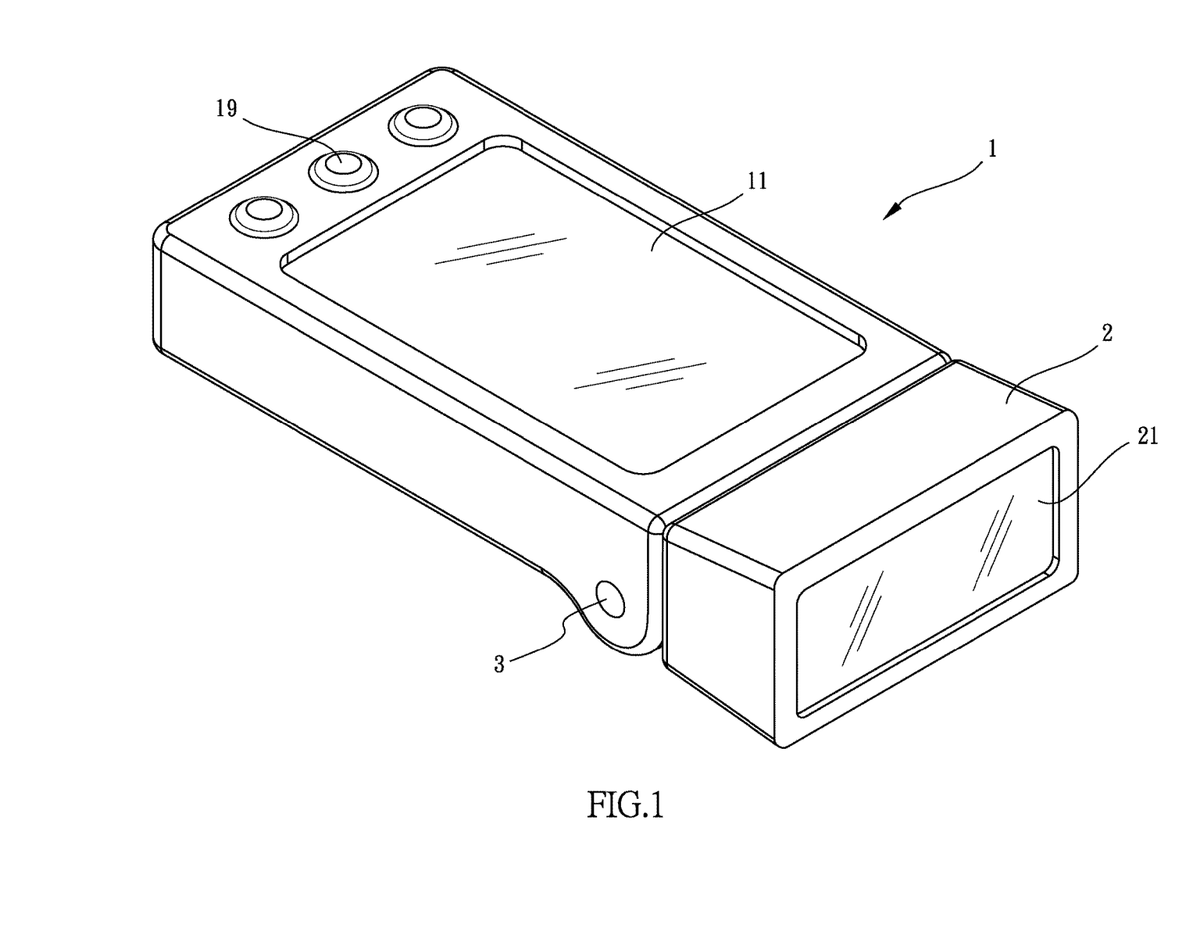
FIG. 1 is a perspective view of a first embodiment of an assembly of a light and a watch of a bicycle capable for adjusting angle of the present invention.
Figure 2:
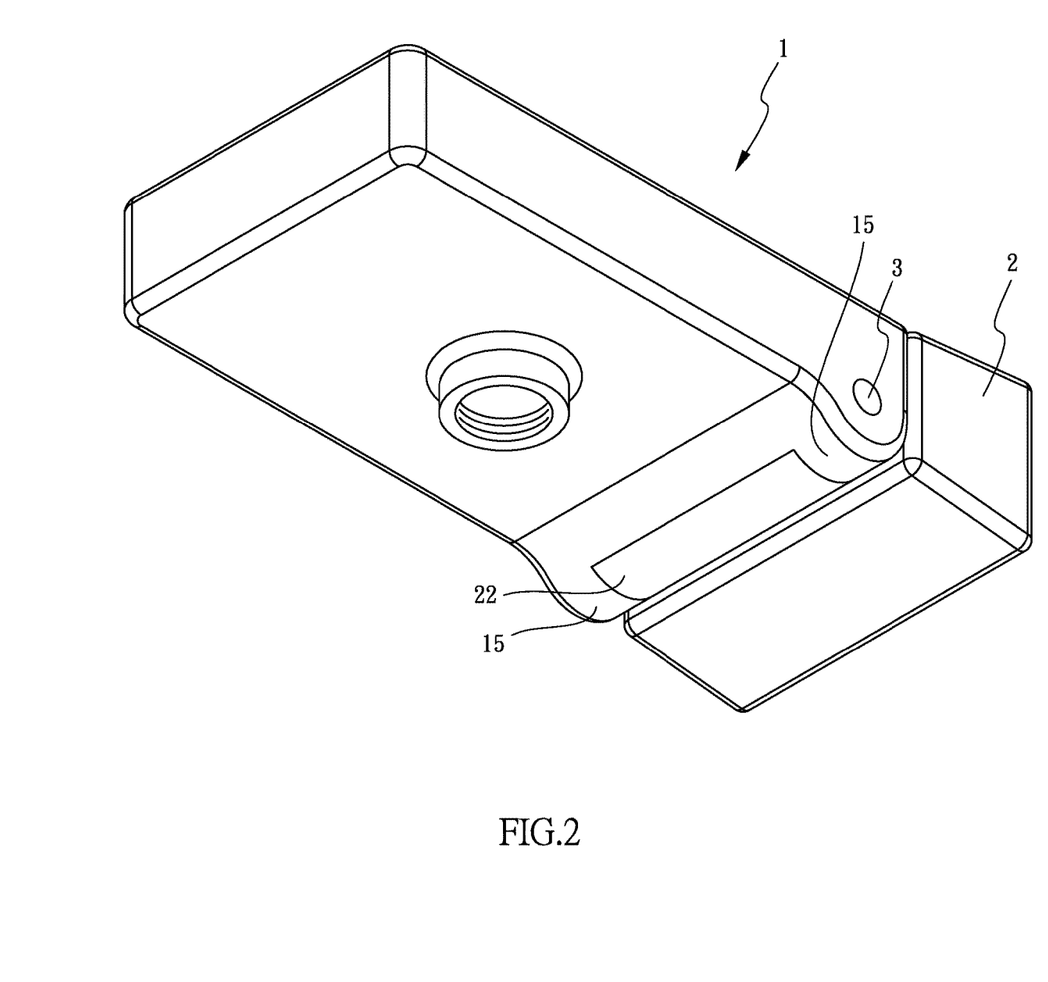
FIG. 2 is a perspective view of the first embodiment of the assembly of the present invention viewed in another angle.
Figure 3:
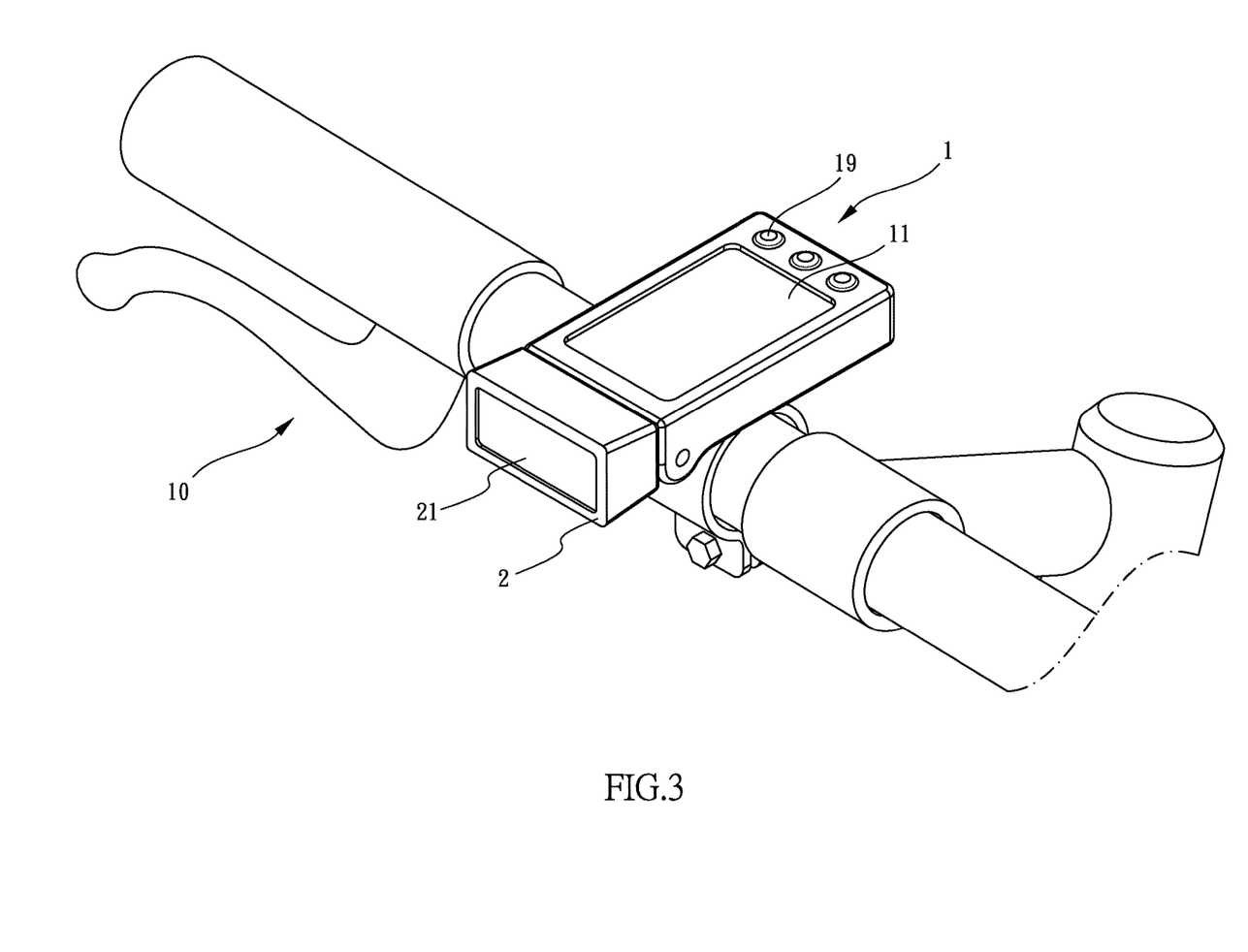
FIG. 3 is a view of the first embodiment of the assembly of the present invention while being mounted on a bicycle.
Figure 4:
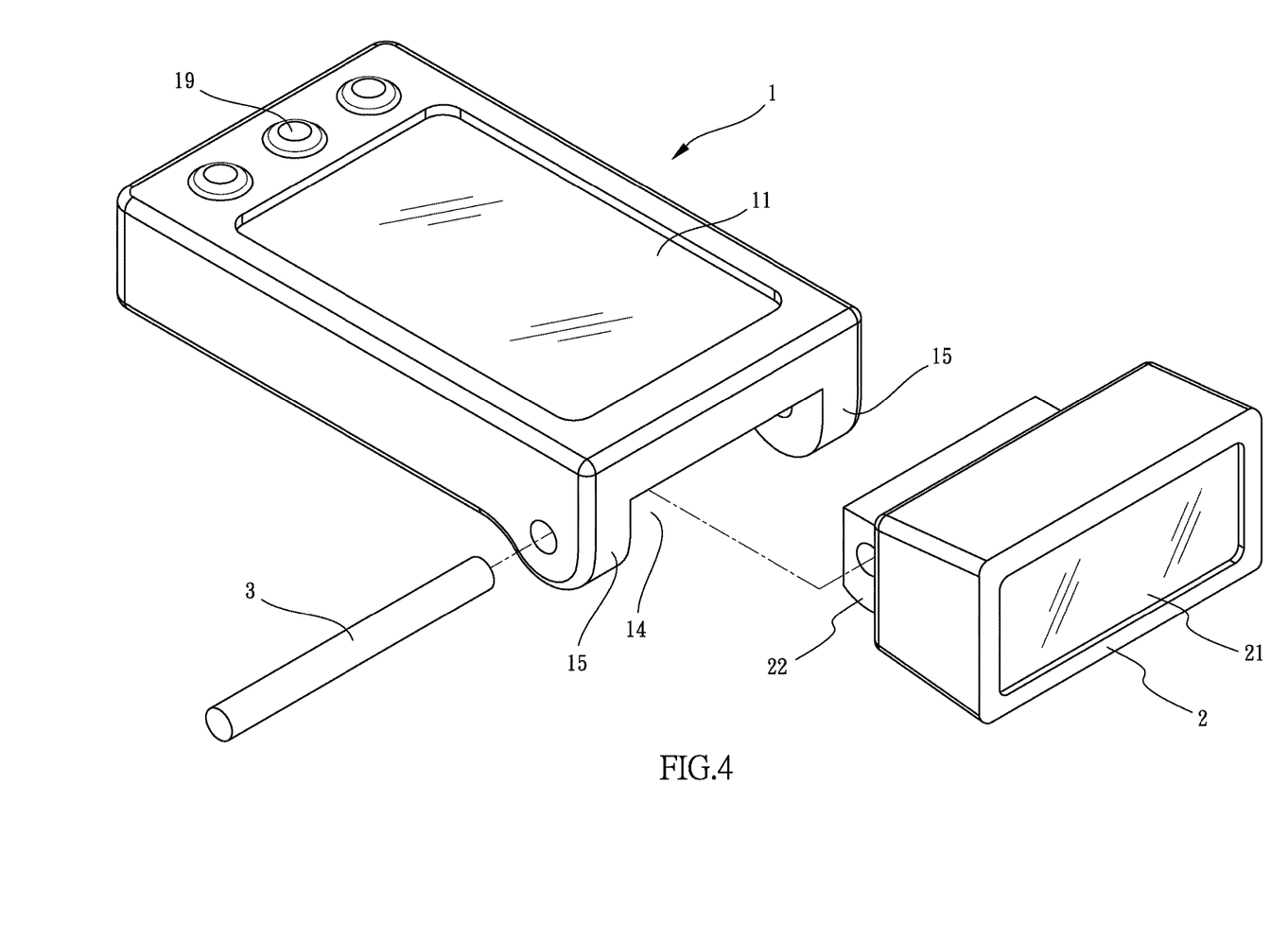
FIG. 4 is a cross-sectional view of FIG. 1.

Consequently, the mount 1 may be mounted on the head of the bicycle 10 by the rider (in FIG. 1, the mount 1 is mounted to a top end of a stein for the main embodiment, but the manners of mounting the mount 1 and the stein are not limited thereto). The rider may see the values or data shown on the display screen 1 to know the operation status of the bicycle 10 and the physical status of the rider to control any situation while riding. In addition, because the light base 2 is pivoted to the front end of the mount 1, the rider may use the light beam transmitted from the light transparent portion 21 of the light base 2 to illuminate forwardly at any time so that the rider may recognize the road conditions and environments in front of the rider at any time and the risk may be reduced due to riding in dark and poor visible place. Besides, because the mount 1 and the light base 2 are assembled to each other, it may make the space of the headset of the bicycle larger and reduce loading so that the rider may not ride too hard but speed up quickly. And the arrangement of the mount 1 may not influence the brake to result in being unable to brake immediately.

Figure 5:
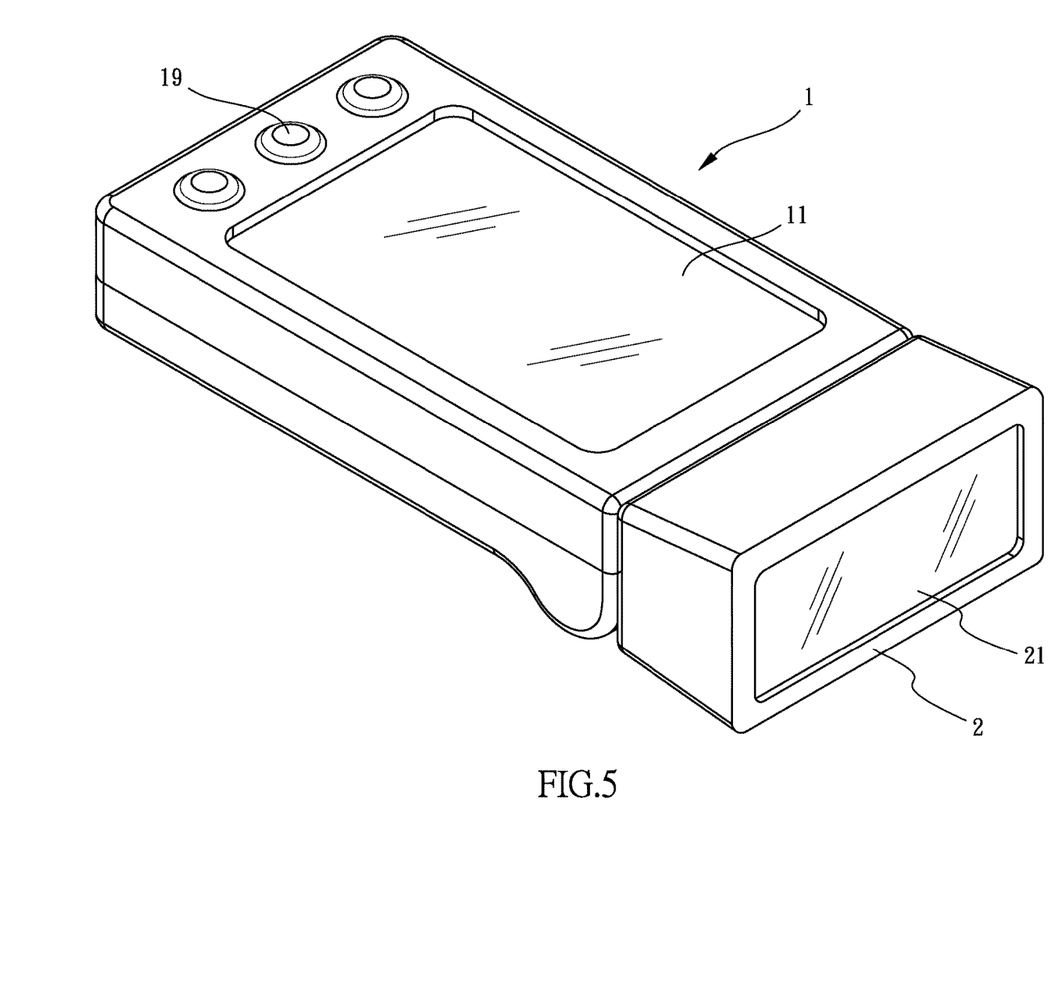
FIG. 5 is a perspective view of a second embodiment of the assembly of the light and the watch of the bicycle capable for adjusting angle of the present invention.
Figure 6:
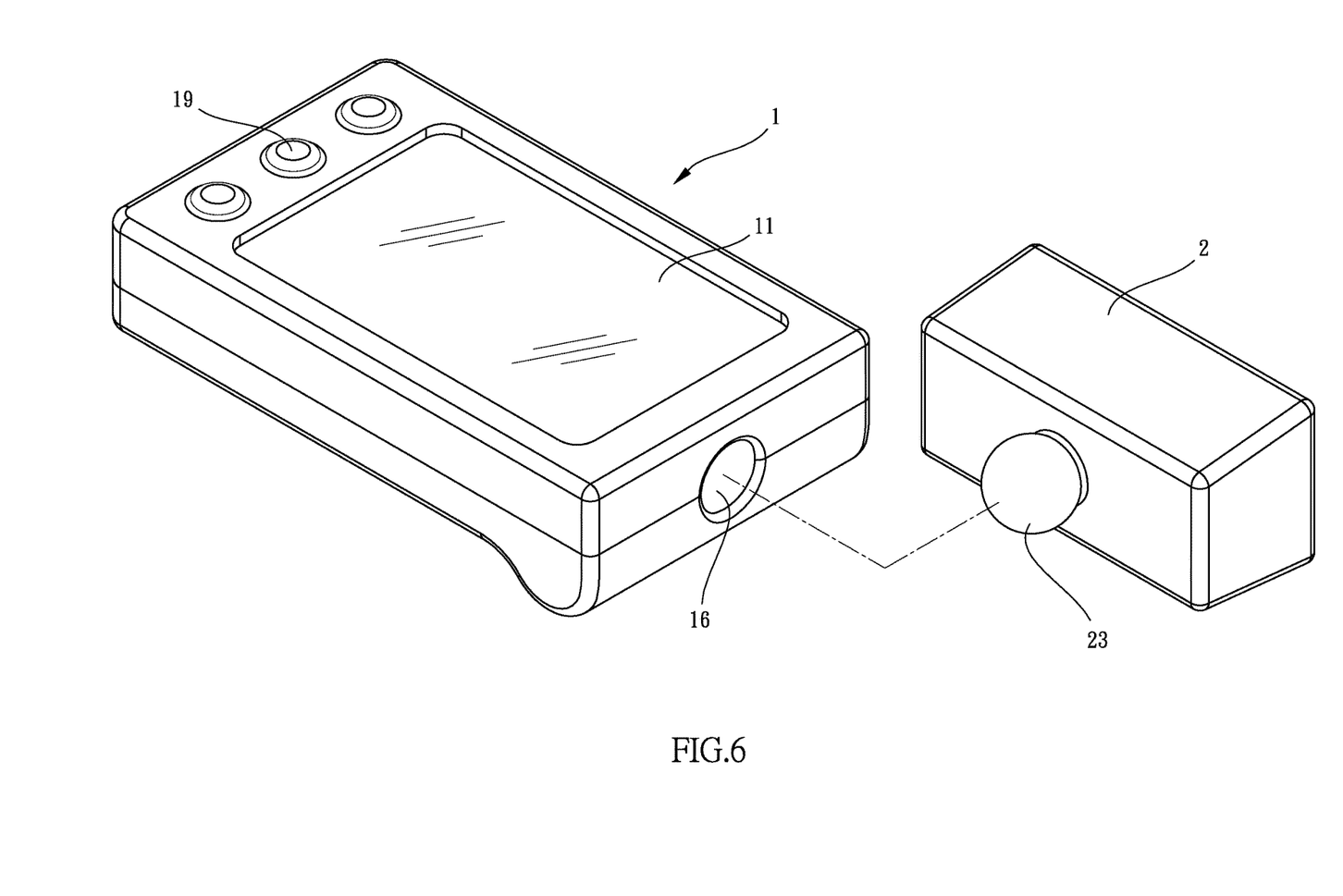
FIG. 6 is a cross-sectional view of FIG. 5.
Figure 7:
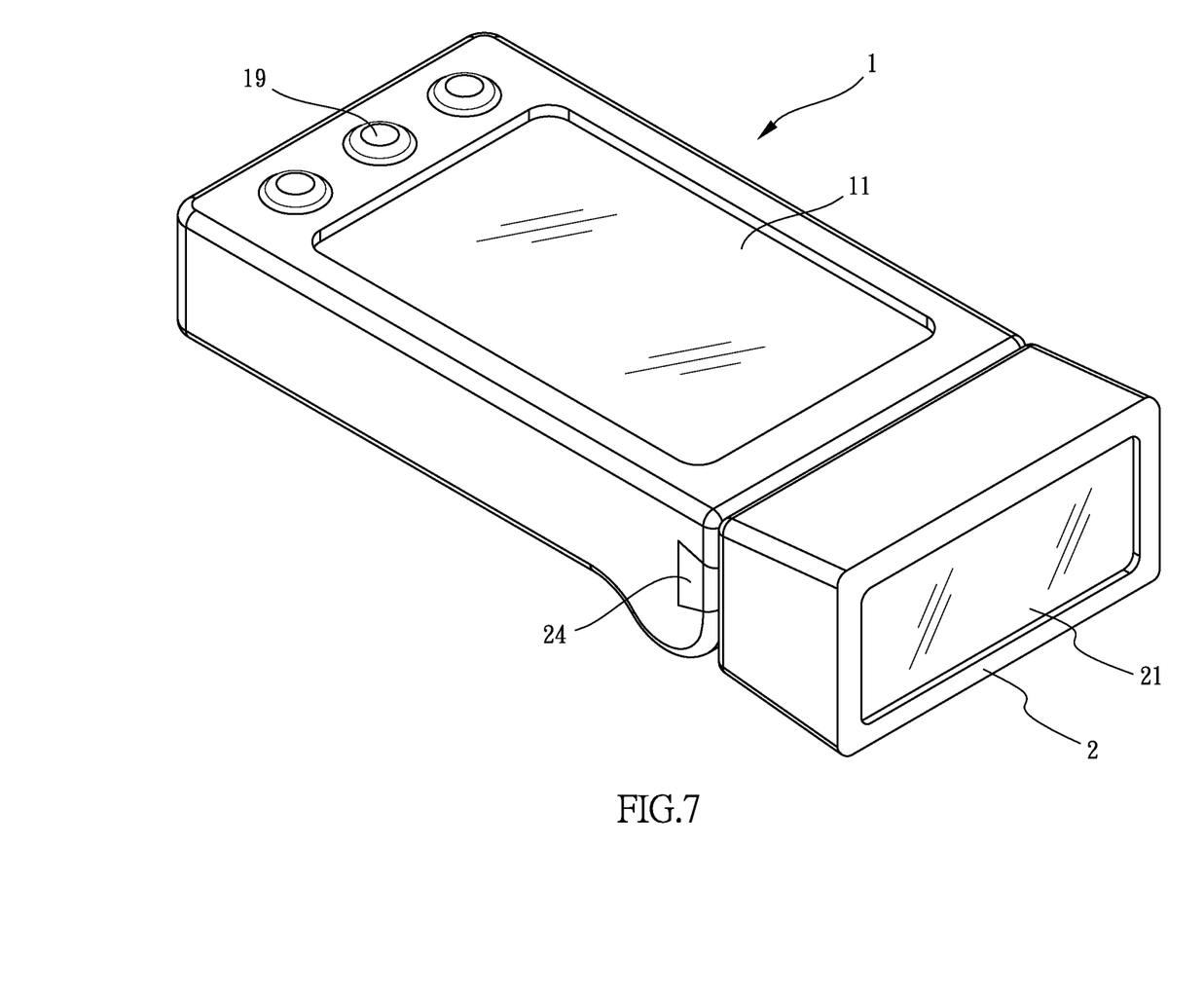
FIG. 7 is a perspective view of a third embodiment of the assembly of the light and the watch of the bicycle capable for adjusting angle of the present invention.
Figure 8:
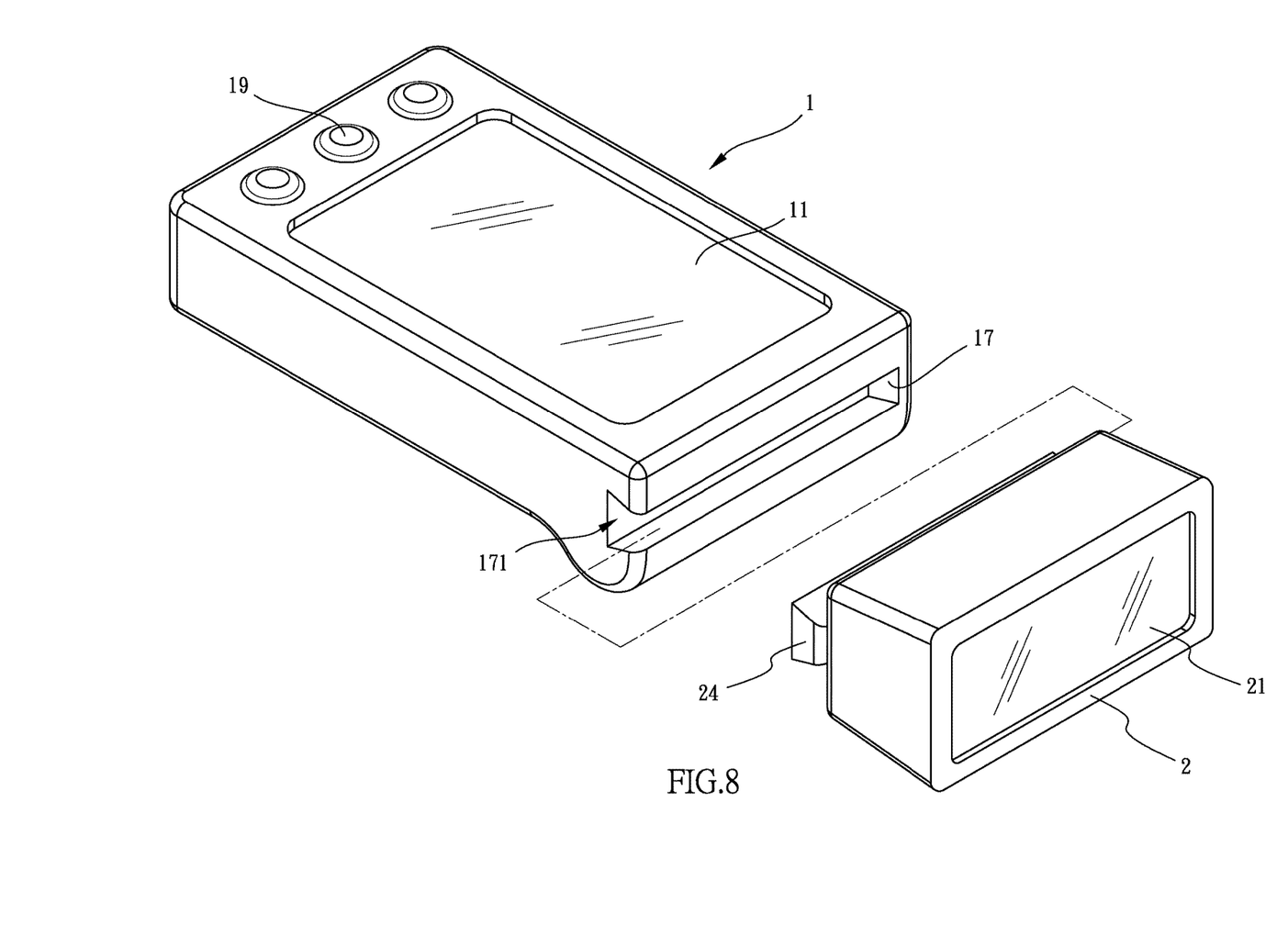
FIG. 8 is a cross-sectional view of FIG. 7.

In order to provide safety while the rider is riding, the manners of assembling the mount 1 and the light base 2 have at least three types. Firstly, please refer to FIGS. 1 to 4, the first embodiment of the present invention is that one end of the mount 1 pivoted to the light base 2 further formed a concave groove 14 and two convex ears 15 which are respectively arranged at two sides of the concave groove 14. One end of the light base 2 corresponding to the concave groove 14 is protruded a pivoting block 22 which is inserted into the concave groove 14. A pin rod 3 is passing through the two convex ears 15 and the pivoting block 22. The pivoting block 22 of the light base 2 is pivoted up and down relative to the concave groove 14 of the mount 1 with the pin rod 3 passing therethrough. Therefore, the light direction of the light beam transmitted from the light transmission portion 21 may be adjusted by the rider. Secondly, please refer to FIGS. 5 and 6, the second embodiment of the present invention is that one end of the mount 1 pivoted to the light base 2 has a ball groove 16. One end of the light base 2 corresponding to the ball groove 16 has a ball embedded block 23. The ball embedded block 23 of the light base 2 is pivoted in the ball groove 16 and the light base 2 is rotated to change direction relative to the mount 1 so that the it may be adjusted in multiple directions to light the environment and road condition by the rider. Thirdly, please refer to FIGS. 7 and 8, the third embodiment of the present invention is that one end of the light base 2 corresponding to the mount 1 is protruded a sliding block 24. One end of the mount 1 corresponding to the light base 2 has a sliding track 17. Any one side surface of the mount 1 corresponding to the sliding track 17 has an opening 171 fluidly communicated with an inside of the sliding track 17. The sliding block 24 of the light base 2 is slid into the sliding track 17 from the opening 171 so that the light base 2 is transversely slid in the mount 1 due to the arrangement of the sliding block 24 and the sliding track 17 and transversely moved to adjust the light position. According to the three embodiments mentioned above, but not limited thereto, it is mainly noted that the light base 2 may be adjusted relative to the mount 1 so that the rider may adjust it to a suitable position based on his/her own favorite and the riding safety may be kept. Therefore, the manners of assembling the mount 1 and the light base 2 may have other types (not shown).

Figure 9:
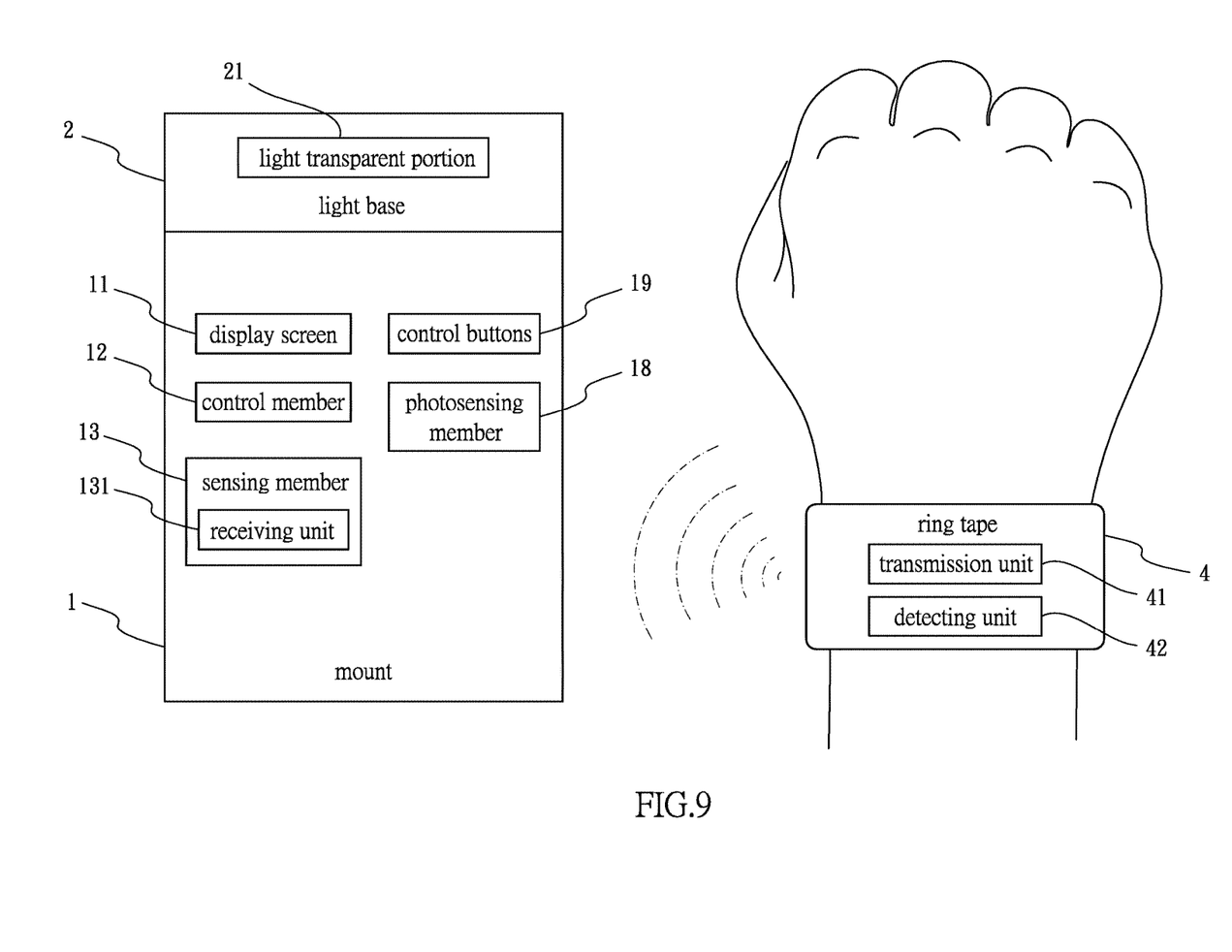
FIG. 9 is a block diagram of the assembly of the light and the watch of the bicycle capable for adjusting angle of the present invention.

Furthermore, besides the light base 2 may be adjusted relative to the mount 1, the light beam in the light base 1 may be also changed. A photosensing member 18 is further arranged in the mount 1 and electrically connected to the control member 12. The photosensing member 18 is detected an ambient luminosity and then activated the control member 12 to control intensity, focusing, and scattering of a light beam transmitted through the light transparent portion 21 of the light base 2. That is, when the photosensing member 18 is detected the intensity of the light source is very weak where the rider stays while riding, the photosensing member 18 is activated the control member 12 to control the light base 2 to emit very bright light for lighting. In contrast, when the photosensing member 18 is detected the light source is brighter where the rider is riding, the photosensing member 18 may be activated the control member 12 to control the light beam of the light base 2 to become weaker. Therefore, it may truly prevent power consumption and further exactly light to truly protect the safety of the rider (shown as FIG. 9).

Figure 10:
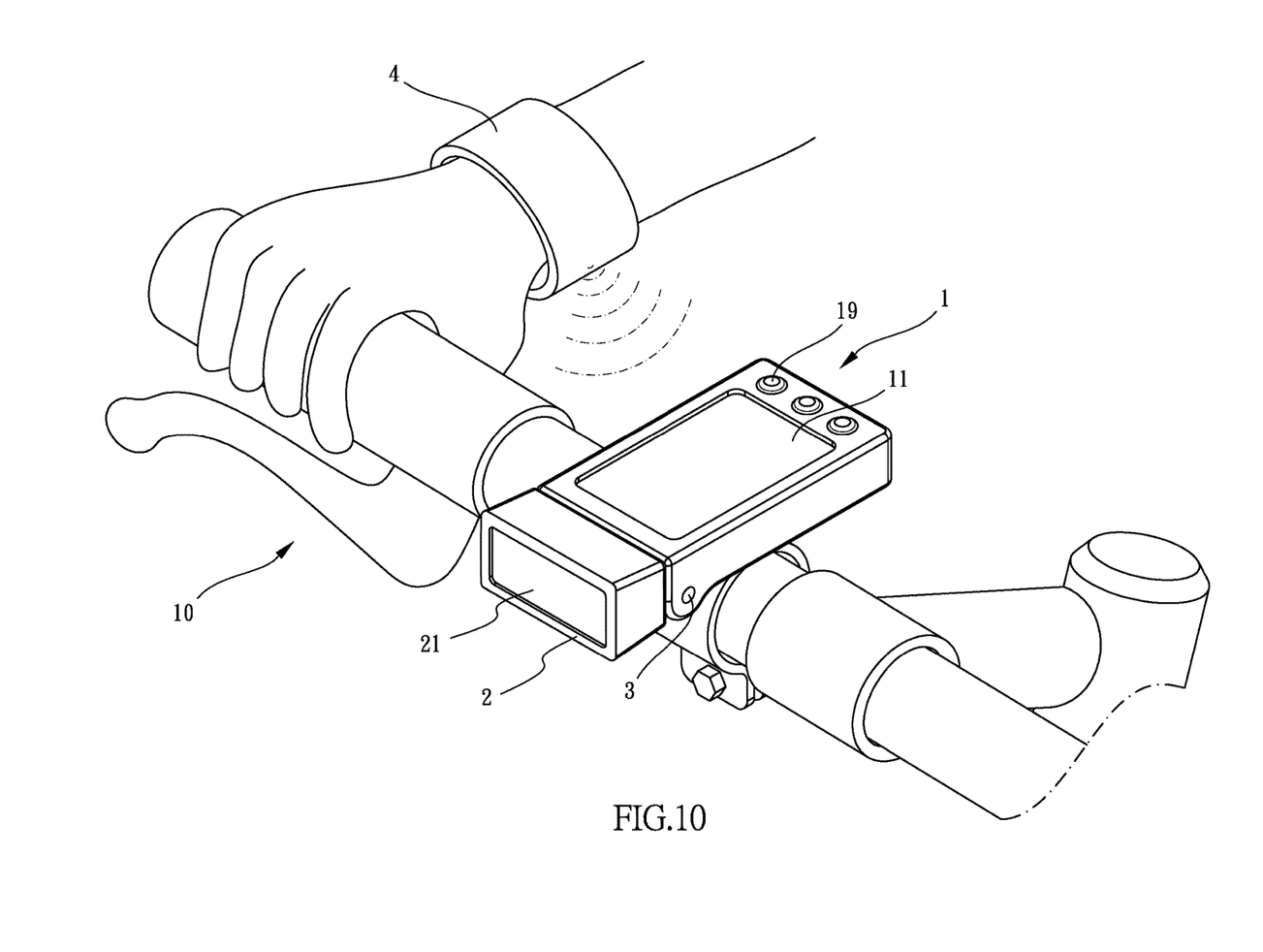
FIG. 10 is a view of the assembly of the present invention while being worn on a rider.

In addition, the above mentioned sensing member 13 arranged in the mount 1 may detect the variation of the operation of the bicycle 10, such as driving distance, revolutions per minute of a gear wheel, tire pressure, and so on. Besides, it may also detect the physical variation of the rider. A receiving unit 131 is built in the sensing member 13 of the mount 1. A ring tape 4 is worn on the rider. A transmission unit 41 and a detecting unit 42 are built in the ring tape 4. When the ring tape 4 is worn on the rider, the detecting unit 42 may be detected a change of the rider's body and transmitted a signal to the receiving unit 131 of the sensing member 13 through the transmission unit 41. When the sensing member 13 is received the signal, it may be transferred and shown on the display screen 11. Therefore, the rider may check his/her own physical condition, such as heartbeat, pulse, calorie, and so on, so that the rider may know his/her own physical condition at any time. The transmission unit 41 is wirelessly transmitted the signal to the receiving unit 131 of the sensing member 13 for receiving and further the received signal is displayed on the display screen 11. The ring tape 4 may be wirelessly communicated with the sensing member 13 (shown as in FIGS. 9 and 10).

Finally, a plurality of control buttons 19 is arranged below the display screen 11 of the mount 1. Each of the control buttons 19 is electrically connected to the control member 12. Each of the control buttons 19 may control, fine tune, and set a value displayed or shown on the display screen 11. The rider may adjust and set the value based on the rider his/her own condition while riding. For example, the rider may set the value displayed or shown on the display screen 11 before riding, such as the calorie after two hours or heartbeat after two hours. It may effectively train the rider. In addition, the control buttons 19 may eliminate the errors shown or displayed on the display screen 11. The control buttons 19 may be set and adjusted before or while riding so that it may be exactly checked and read (shown as in FIG. 1).

In conclusion, the assembly of the present invention may be mounted on the top end of the stein of the bicycle 10 to make the end of the mount 1 having the display screen 11 face the rider and the light transparent portion 21 of the light base 2 may face the direction in front of the bicycle 10 before riding. The rider may check or read the value (or information) shown or displayed on the display screen 11, such as speed per hour, time, kilometer, revolution per minute of the wheel, and heartbeat of the rider or calorie so as to enjoy riding and pay attention to his/her own and the bicycle's condition at the same time. It may achieve the effect of exercising. The light base 2 may provide suitable lighting. The rider may adjust the lighting direction of the light beam transmitted from the light transparent portion 21 of the light base 2 and the intensity of the light beam transmitted from the light transparent portion 21 may be changed by detecting the brightness of the ambient light source according to the arrangement of the light base 2 and the mount 1. It may make the rider protect his/her own safety from riding in dark and poor visible place by lighting the road condition and environment in front of the bicycle 10 with the light beam transmitted from the light transparent portion 21. It is not only cable for recognizing, but also others may clearly see the rider who stays at the position having the light source to prevent from colliding with each other and resulting in dangers. The safety of the rider and others may be protected. Compare to the prior art, the present invention may have non-obviousness to a certain extent.

The foregoing descriptions are merely the exemplified embodiments of the present invention, where the scope of the claim of the present invention is not intended to be limited by the embodiments. Any equivalent embodiments or modifications without departing from the spirit and scope of the present invention are therefore intended to be embraced.

The disclosed structure of the invention has not appeared in the prior art and features efficacy better than the prior structure which is construed to be a novel and creative invention, thereby filing the present application herein subject to the patent law.

What is claimed is:

1. An assembly of a light and a watch of a bicycle capable for adjusting angle, comprising:

a mount, one side of the mount mounted on the bicycle, a display screen arranged at a top surface of the mount, a control member and a sensing member arranged in the mount and electrically connected with the display screen, the sensing member detecting a variation of a rider and the bicycle to display on the display screen; and a light base, one side thereof being pivoted relative to a front end of the mount and the other end thereof having a light transparent portion, the light base being pivoted, rotated, and slid relative to the mount, the light base electrically connected with the control member, and the control member controlling a variation of a light beam of the light base;

wherein the mount is mounted on the bicycle so that the rider may see a display on the display screen and it is convenient to provide for lighting;

wherein one end of the mount pivoted to the light base is formed a concave groove and two convex ears are respectively arranged at two side of the concave groove, one end of the light base pivoted to the mount protrudes a pivoting block which is inserted into the concave groove, a pin rod passes through the two convex ears and the pivoting block, and the pivoting block of the light base is pivoted up and down relative to the concave groove with the pin rod passing therethrough, and wherein a receiving unit is built in the sensing member of the mount, a ring tape is worn on the rider, a transmission unit and a detecting unit are built in the ring tape, the detecting unit detects a change of the rider's body and transmits a signal to the receiving unit of the sensing member through the transmission unit, the transmission unit wirelessly transmits the signal to the receiving unit of the sensing member, the received signal by the receiving unit is displayed on the display screen.

2. The assembly as claimed in claim 1, wherein a photosensing member is further arranged in the mount and electrically connected to the control member, the photosensing member is detected an ambient luminosity and then activated the control member to control intensity, focusing, and scattering of a light beam transmitted through the light transparent portion.

3. The assembly as claimed in claim 1, wherein a plurality of control buttons is arranged below the display screen, the control buttons are electrically connected to the control member, and each of the control buttons may control, fine tune, and set a value displayed on the display screen.

* * * * *